United States Patent
Basaglia

(10) Patent No.: US 8,905,959 B2
(45) Date of Patent: Dec. 9, 2014

(54) MEDICAL APPARATUS COMPRISING A MACHINE FOR TREATMENT OF FLUIDS

(75) Inventor: Gianni Basaglia, Mirandola (IT)

(73) Assignee: Gambro Lundia AB, Lund (SE)

( * ) Notice: Subject to any disclaimer, the term of this patent is extended or adjusted under 35 U.S.C. 154(b) by 681 days.

(21) Appl. No.: 12/935,851

(22) PCT Filed: Apr. 2, 2009

(86) PCT No.: PCT/IB2009/005161
§ 371 (c)(1),
(2), (4) Date: Sep. 30, 2010

(87) PCT Pub. No.: WO2009/122270
PCT Pub. Date: Oct. 8, 2009

(65) Prior Publication Data
US 2011/0028881 A1    Feb. 3, 2011

(30) Foreign Application Priority Data
Apr. 4, 2008   (IT) ............... MI2008A0584

(51) Int. Cl.
*A61M 37/00*   (2006.01)
*A61M 1/14*   (2006.01)
*A61M 1/34*   (2006.01)
*A61M 1/36*   (2006.01)
*G06F 19/00*   (2011.01)

(52) U.S. Cl.
CPC . *A61M 1/14* (2013.01); *A61M 1/34* (2013.01); *A61M 1/36* (2013.01); *G06F 19/3481* (2013.01); *A61M 2205/35* (2013.01)
USPC ...................................... 604/4.01

(58) Field of Classification Search
CPC ....... A61M 1/14; A61M 1/16; A61M 1/1601; A61M 1/1603; A61M 1/1605; A61M 1/1607; A61M 1/1609; A61M 1/1611; A61M 1/1615; A61M 1/1617; A61M 1/1619; A61M 1/34; A61M 2205/35; G06F 19/3481
USPC .................. 604/4.01–6.16; 700/90; 705/2–3; 715/771
See application file for complete search history.

(56) References Cited

U.S. PATENT DOCUMENTS

| 5,885,245 | A | 3/1999 | Lynch et al. |
| 7,044,927 | B2 | 5/2006 | Mueller et al. |
| 2002/0082728 | A1* | 6/2002 | Mueller et al. .................. 700/90 |
| 2004/0220832 | A1* | 11/2004 | Moll et al. ......................... 705/2 |
| 2005/0108709 | A1 | 5/2005 | Sciandra et al. |
| 2008/0154177 | A1* | 6/2008 | Moubayed et al. ............. 604/19 |
| 2008/0195777 | A1 | 8/2008 | Dickens et al. |

FOREIGN PATENT DOCUMENTS

| EP | 1 195 708 A1 | 4/2002 |
| EP | 1 956 832 A2 | 8/2008 |

* cited by examiner

Primary Examiner — Philip R Wiest
(74) Attorney, Agent, or Firm — Pearne & Gordon LLP

(57) ABSTRACT

A medical apparatus comprises a machine for treatment of fluids provided with means (3) for treating a patient's blood which exhibit a control unit (4) for sending command signals and receiving information relating to the treatment under way on the patient. A remote unit (7) is included which enable the remote unit (7) to selectively take control of a predetermined number of functions of the medical machine. The control unit (4) of the medical machine is predisposed to selectively inhibit the remote control means (10) from taking or maintaining control of the functions of the medical machine in consequence of the operating configuration of the machine.

35 Claims, 3 Drawing Sheets

MEDICAL APPARATUS COMPRISING A MACHINE FOR TREATMENT OF FLUIDS

BACKGROUND OF THE INVENTION

The invention relates to a medical apparatus and in particular a machine for extracorporeal treatment of a fluid, i.e. a patient's blood.

As is known, machines for treatment of blood, such as for example machines for treatment of kidney failure or liver insufficiency or machines for plasmapheresis, i.e. machines for other types of fluid treatment, are provided with special means for treating a fluid in general comprising appropriate sensors and actuators which enable the cited treatment to be carried out.

In general all the above-mentioned machines have in common a presence of a control unit which is destined to send control signals and to receive data from the sensors and/or actuators for monitoring and controlling the treatment.

Obviously for interaction with the machines, the operator can provide commands to the control unit, as well as view machine data and parameters in order to monitor its functioning.

To this end, usually at least a device for entering data is included which can be constituted by a keyboard, a mouse, suitable buttons and activations, or even a touch screen; there is also always a special display for visualising the data requested received from the sensors and/or relating to the actuators.

Over time, and with developments in information technology, it has also become possible to memorise and transfer a plurality of machine operating data which, if entered in a computer network, can be sent to a central server and thereafter be read, processed and analysed with the aim of improving the treatment, controlling machine functioning to make sure it is correct. It also provides the chance to compare the immense amount of data provided for reasons of research, for compiling statistics or for other purposes besides.

The type of infrastructure described above gives remote and totally passive access to machine data and patient data, i.e. it does not enable a real interaction between the remote user and the machine itself.

In order at least partially to resolve this drawback, document U.S. Pat. No. 5,885,245 teaches use of a medical apparatus in which a special device for treatment of a fluid is positioned in a first location and is able, via a dedicated modem and a special telephone line, to communicate with a remote control device which is in turn able to receive and transmit data to the medical apparatus via a corresponding modem and use of the cited telephone line.

In more detail, the medical apparatus of the prior document comprises an infusion pump which can be directly controlled by the operator in the place where the apparatus is in use, by means of a display which visualises the functioning parameters and a keyboard for entering the necessary commands.

The remote control unit is provided with a corresponding display for remote viewing of the same data relating to the medical apparatus and can be used for monitoring the operativity of the infusion pump, but also for controlling it.

In other words the remote device enables four basic functions to be carried out, comprising the control of the infusion pump, the monitoring of the pump, the transmission of data from the infusion pump to the remote control unit, as well as the viewing of the pump data on the remote device.

All of the above is carried out via a normal telephone line with a special dedicated transmission protocol which can set the medical apparatus and the control device in communication.

It can be seen how the briefly-described above device has constituted progress with respect to the simple transmission of data for a subsequent analysis without any chance of intervening from afar on the machine; however the illustrated apparatus reveals itself to be affected by some drawbacks and is susceptible to improvement under various aspects.

The devices in the prior art are in fact very poorly flexible and not sufficiently user friendly.

Also from the point of view of safety, the only effective measure is linked to the use of a dedicated protocol which reduces the risk that an unauthorised third party might take remote control of the medical apparatus, with consequent serious damage which this might lead to.

In any case the person in possession of the remote control device can intervene improperly on the medical machine.

AIM AND SUMMARY OF THE INVENTION

An aim, therefore, of the present invention is substantially to resolve all the above-cited drawbacks.

A first aim of the invention is to provide a medical apparatus which can be remote-controlled and which can guarantee high safety standards without causing the network architecture to become over-complex.

A further aim of the invention is to allow remote access for only monitoring and/or control intuitively, simply and with the most universal modalities possible, i.e. without requiring special ICT capacities or dedicated remote applications/devices.

These and other aims which will better emerge during the course of the present description are substantially attained by the medical apparatus described in the accompanying claims.

BRIEF DESCRIPTION OF THE DRAWINGS

Further characteristics and advantages will better emerge from the detailed descriptions that follow of a preferred though not exclusive embodiment, in agreement with the accompanying figures of the drawings, in which.

DETAILED DESCRIPTION OF SOME PREFERRED EMBODIMENTS

With reference to the cited figures, 1 denotes in its entirety a medical apparatus. In particular, the medical apparatus comprises at least one and in general a plurality of medical machines 2 for fluid treatment.

The machine can be, for example, a machine for blood treatment, such as a machine for treatment of kidney failure (for example a hemo(dia)filtration machine or a hemodialysis machine, for chronic or intensive therapy) or liver insufficiency or a plasmapheresis machine or in any case any other type of medical machine suitable for treatment of a fluid.

In the following description, reference will be made to a machine for extracorporeal treatment of blood in its essential components of known type and only partially mentioned.

The apparatus for fluid treatment comprises means for blood treatment 3.

In particular, the means 3 comprise a hydraulic circuit 100.

Figure 1:
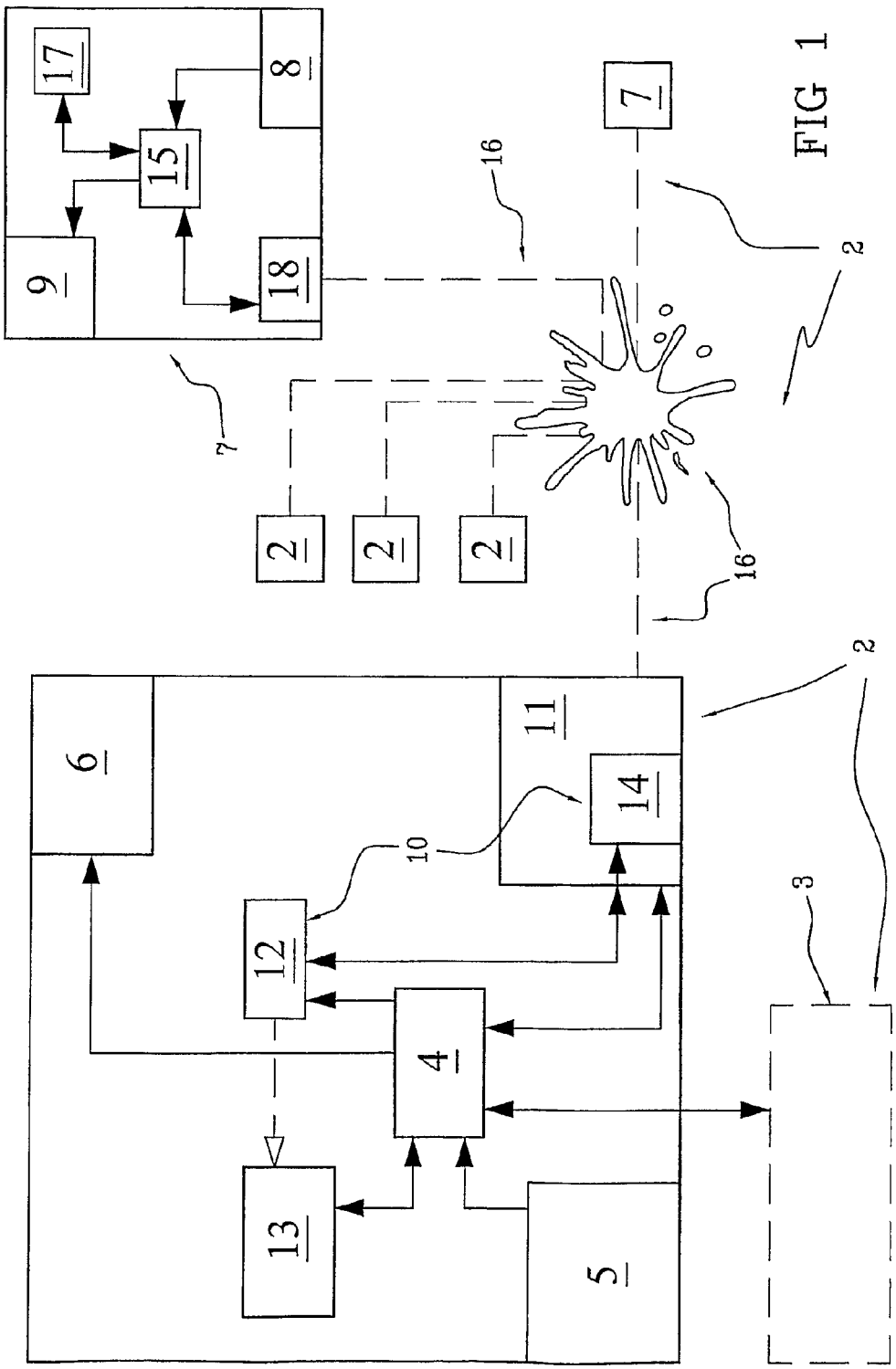
FIG. 1 schematically illustrates a medical apparatus of the present invention, in which the medical machine is monitored/controlled by a remote unit.
Figure 2:
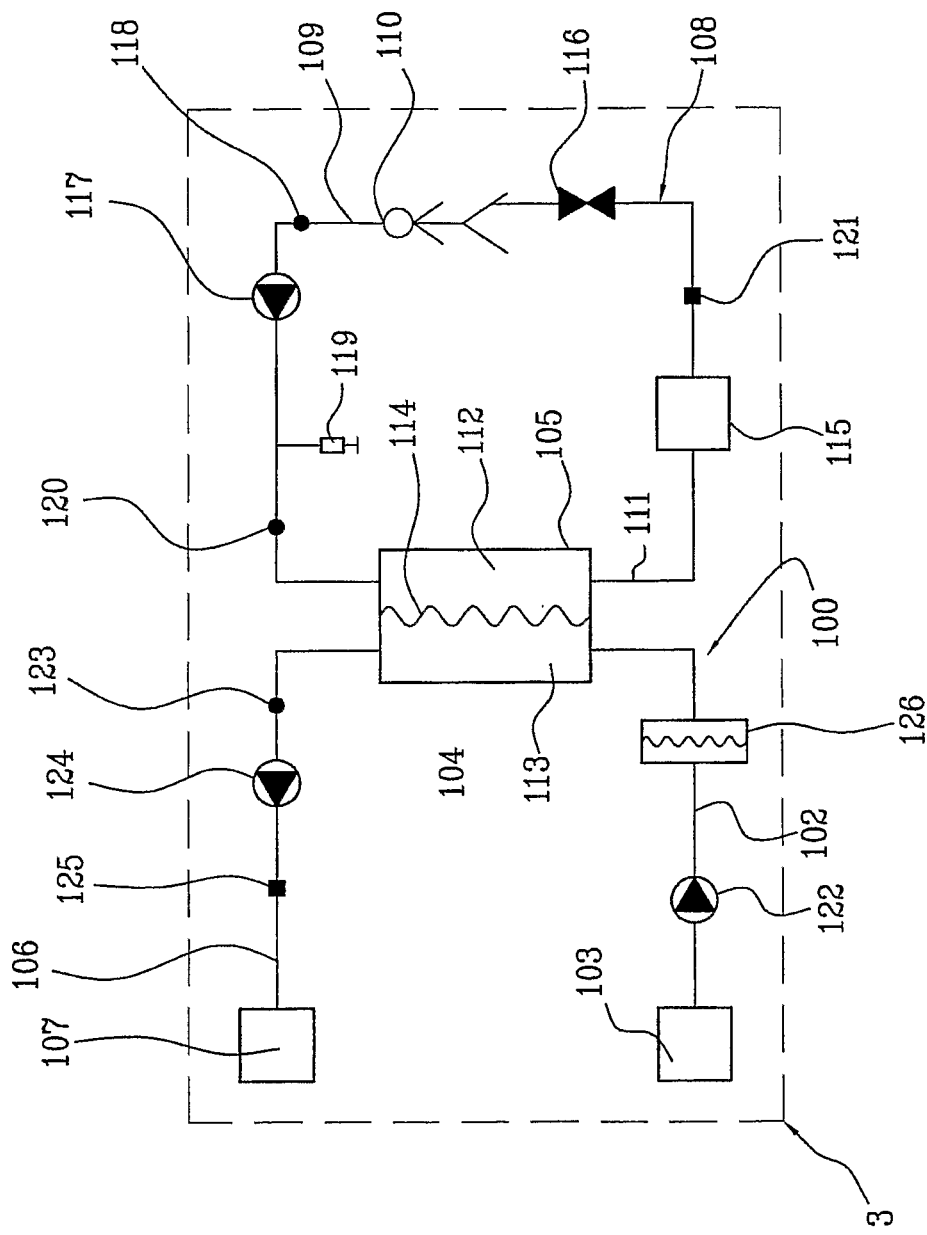
FIG. 2 illustrates a schematic view, by way of example, of means for treating a fluid, part of the medical machine of FIG. 1.

An example of a realisation of a hydraulic circuit is schematically illustrated in FIG. 2.

Note that the specific structure of the hydraulic circuit 100 is not relevant to the ends of the present invention and that therefore circuits which are different from the one specifically shown in FIG. 2 might be used according to the functional and design requirements of each single medical apparatus.

The hydraulic circuit 100 optionally exhibits at least a supply channel 102, destined for transport of a treatment liquid from at least a source 103 towards a treatment station 104 where one or more blood treatment units 105 operate.

The circuit 100 further comprises at least a discharge channel 106 destined to transport a used liquid from the treatment station 104 towards an evacuation zone, schematically denoted by 107 in FIG. 2.

It should be noted that the supply channel 102 is destined to cooperate with means for moving a fluid, such as at least a pump 122, for example a positive displacement pump, such as in particular a peristaltic pump, or a gear or diaphragm pump.

A branch can be present downstream of the pump 122 and along the circulation direction, which divides the primary sterile fluid circuit into an inlet branch and an infusion branch (not illustrated but of known type).

The infusion branch is connected to the blood removal line (arterial line) and/or the blood return line (venous line) of the blood circuit and enables an infusion to be obtained directly into the blood (before and/or after the blood treatment unit 105) using sterile fluid.

The input branch brings the sterile fluid directly to the blood treatment stations 104 for exchange through the membrane 114.

Obviously selector means (for example a valve element and/or means for moving, such as one or more pumps) will be present for determining the percentage quantities of fluid flow in the infusion branch and the entry branch.

The sterile fluid for dialysis thus enters the discharge channel 106 of the circuit and crosses a pressure sensor 123 provided for control of the functioning of the line.

There are therefore further fluid movement means present, for example a drainage pump 124 which can control the flow in the discharge channel 106 of the circuit.

The drainage pump 124 can, in general, be a positive displacement pump, such as for example a peristaltic pump, or a gear pump, or a diaphragm pump.

The fluid to be eliminated thus crosses a blood leak detector 125 and is conveyed towards the evacuation zone 107.

The treatment fluid (dialysis fluid or replacement fluid) can be purified before use by one or more ultrafilters 126.

The hydraulic circuit 100 cooperates with a blood circuit 108 which is also schematically represented in FIG. 2 in its basic components.

The specific structure of the blood circuit is also not fundamental with reference to the present invention, and thus, with reference to FIG. 2, a brief description of a possible embodiment of the circuit is provided, which should however be considered to be provided purely by way of non-limiting example.

The blood circuit 108 of FIG. 2 comprises an arterial line 109 for removing blood from a vascular access 110 of a patient and a venous line 111 predisposed to return the treated blood to the vascular access.

The blood circuit of FIG. 2 further comprises a first chamber, or blood chamber 112, of the blood treatment unit 105 whose second chamber 113 is connected to the hydraulic circuit 100.

In greater detail, the arterial line 109 is connected to the inlet of the blood chamber 112, while the venous line 111 is connected in outlet to the blood chamber 112.

In turn, the supply channel 102 is connected in inlet to the second chamber 113, while the discharge channel 106 is connected in outlet to the second chamber.

The blood treatment unit 105, for example a dialyser or an ultrafilter or a plasma filter or a hemofilter or a hemodiafilter, comprises, as mentioned, the two chambers 112 and 113, which are separated by a semi-permeable membrane 114, for example a hollow-fibre or plate-type membrane.

A blood pressure sensor 118 is located on the arterial line 109 along the circulation direction of the blood from the removal zone (vascular access) towards the blood treatment unit 105. The arterial line 109 is further connected to a device for administering an anticoagulant 119, for example a syringe pump for providing appropriate anticoagulant doses (heparin).

The arterial line can thus be provided, optionally, with a further pressure sensor 120 (arranged between a pump 117 and the unit 105) for surveying the correct flow internally of the blood circuit.

The blood circuit can also comprise one or more air separators 115: the example of FIG. 2 shows a separator 115 on the venous line 111, upstream of a safety valve 116.

The treated blood, exiting from the air separator device 115, crosses an air bubble sensor 121, provided to check for the absence of dangerous formations internally of the treated blood which must be returned into the patient's blood circuit.

In particular, should the air bubble sensor reveal the presence of faults in the blood flow, the machine, via the safety valve 116 (which might be a cock, a clamp or the like) it would be able immediately to block blood passage in order to prevent any type of consequence to the patient.

The valve 116 can always be closed in the venous line should, for example for safety reasons, it become necessary to interrupt blood return to the vascular access 110.

The means 3 for fluid treatment can also comprise one or more blood pump 117, for example positive displacement pumps such as peristaltic pumps; in the example of FIG. 2 there is a pump 117 on the arterial line 109.

In general, the hydraulic circuit 100 is housed internally of a chamber in the machine body, while the blood circuit 108 is borne on a front panel of the machine body which also supports the peristaltic pump or pumps 117.

The treatment unit 105 can be removable physically supported, by rapid-attachment means (of known type) arranged, for example, on a lateral wall of the machine structure itself. The treatment unit 105, in operating conditions of blood treatment, is connected both to the hydraulic circuit and to the blood circuit as already briefly mentioned.

As is obvious and indeed known, the means 3 for fluid treatment comprise the cited sensors for detecting functioning parameters of the medical machine 2 and also the cited actuators for intervening in order to modify the functioning parameters of the machine 2.

Each medical machine 2 in general comprises a control unit 4 which is programmed at least to send command signals and to receive data from the means 3 for fluid treatment.

The control unit 4 is thus active at least on the blood circuit and in particular on the pressure sensor 118, on the blood pump 117, on the heparin infusion device 119, on the further pressure sensor 120 as well as on the device for detecting the presence of air bubbles 121 and on the closing element 116.

The control unit 4 will be active on the pump 122, on any selector means present, on the pressure sensor 123, on the drainage pump 124 and will also receive information from the blood leak detector 125.

Further, the control unit 4 is set up to control the hydraulic circuit 100 of the sterile fluid and in particular will receive in input the data read off by any balances present on the machine relating to the weight of the various containers which may be in use on the machine.

Obviously, apart from the control of the sensors and the actuators, the control unit 4 may be predisposed to receive and control further sensors and actuators present on the machine in order to guarantee and monitor the functioning thereon.

The machine for extracorporeal treatment may be provided with a fluid balance system, of the type used in a machine for hemodialysis and hemo(dia)filtration, for control of the patient's weight loss during the treatment, for example a flow-meter type, or a variable-volume volumetric chambers system, or a system including balances, or other systems of known type.

The machine can be provided with a system, of known type, for on-line preparation of the treatment fluid (for example dialysis fluid and/or replacement fluid) starting from water and concentrates, and/or a system (of known type) for degassing and/or heating the fluids running through the system itself, and/or a purification system having one or more treatment fluid ultrafiltration stages.

The machine can be provided with a disinfection/cleaning system (of known type, for example of a chemical or thermal type, supplied by a distribution network or a batch source of disinfecting agents/cleaners) of the hydraulic circuit 100.

Purely by way of example there might also be a liquid loss sensor destined to detect any eventual breakages or damage to the hydraulic circuit, which sensor will then send the data on directly to the control unit 4 for subsequent processing.

The control unit 4 can, for example, comprise one or more digital microprocessing units or one or more units of an analog and/or digital type.

In practice, in reference to the example of a microprocessor unit, once the unit has completed a special program (for example a program coming from outside the system or directly installed on the microprocessor), it is programmed by defining a plurality of functional modules or blocks which constitute means each predisposed to perform respective operations.

The medical machine is provided with at least a display 6 for viewing at least a part of the data received from the control unit 4 relating to the means for fluid treatment.

Further, the medical machine will be provided with at least one and in general a plurality of devices 5 for entering the data to be supplied to the control unit 4 in order to enable a user to generate the above-mentioned command signals for the means 3 for fluid treatment.

The devices for entering data can be of various natures and be constituted, even in combination, by a keyboard, a mouse, keys and buttons and activations, or even a touch screen.

In particular the display or screen of the medical machine 2 displays a graphic user interface (GUI) which provides an intuitively-comprehensible display of at least a part of the data received from the control unit 4 relating to the sensors and the actuators on the fluid treatment circuit.

Merely by way of non-limiting example, in a case in which a graphic user interface is used with a configuration of the touch screen, the display 6 itself will be divided into various areas exhibiting a plurality of touch keys and a plurality of pictograms, each for example associated to a relative touch key.

The expression "touch screen" relates to a screen for data output, also used for input by means of direct selection using the fingers of parts (touch keys) of the screen display to send the commands for performing the user's requested action to the control unit 4.

The use of a touch screen might for example configure the display and the device 5 for entering the data in a single element.

The main aim of a touch-screen display is that it makes the interface more intuitively simple use for the operator, and at the same time simplifies the use of the machine.

The medical apparatus advantageously also exhibits remote access and control means 10 which can enable a remote unit 7 to accede to data present in the medical machine and selectively take over control of a predetermined number of functions of the medical machine itself.

In general the remote access and control means 10 comprise at least a central control program 12 for enabling remote administration of the functions of the medical machine; the central control software 12 can be a VNC type program, and in particular a VNC server program.

In general, VNC programs (Virtual Network Computing) are open source with remote control and serve for remotely administrating a machine.

The VNC server will cooperate with the control unit 4 which, once the program has been run, will be programmed to define the access and control functions from a remote position.

Purely by way of example, the VNC server can be pre-stored on a memory bank 13 of the medical machine to which the control unit 4 will be able to accede. Obviously the remote access and control means 10 will also comprise client control software 14 for interacting with the central control program 12 in order to enable the mentioned data exchange between the control unit 4 and the remote unit 7.

The client control software 14 will also optionally be of the VNC type and in particular VNC client.

Note that while the VNC server will in general be stored internally of the medical machine, the VNC client might be differently located.

The VNC client might for example be directly loaded on the remote control unit 7 which might be an electronic processor such as a computer, but also a hand-held computer or a smart-phone.

Alternatively the VNC client might be directly installed in an intermediate server, to which the remote unit 7 will accede and which in turn will initiate the communication with the medical machine.

In a preferred embodiment it will also be possible for the VNC client to be loaded directly in the medical machine 2 such that it is possible to accede to monitoring and control functions remotely by using a remote control unit 7 without any type of dedicated software, for example a normal processor, a hand-held unit or a smart-phone, as long as it is on-line with the medical machine to be controlled and/or monitored.

For this purpose the medical machine will be provided with a web server 11 operatively cooperating with the control unit 4.

In general a web server is a program which on request of a browser 18 requests one or more web pages (often written in HTML).

A web server is also usually (though not necessarily) provided with a fixed IP address on the net such as to be able to gain remote access more simply.

The data sent from the web server travel in a processor network, transported by the cited http protocol (or equivalent protocols).

The web server 11 of the medical machine 2 is configured to provide a predetermined number of remotely-accessible web pages via the connecting means 16. The web server 11 can contain the predetermined number of web pages or it can generate them at the necessary moment and send them.

In particular the web server 11 can generate these web pages in real time and can therefore transmit them to a user (for example via the connecting means 16), particularly on request of the user him or herself. This enables system security to be increased, especially because it prevents undesired breaches by hackers onto any pages stored in a memory. In effect the web server 11, in order to reduce the risk of fraudulent break-ins from the outside, might not necessarily operate by storing data (web pages), but via generation on demand (in real-time) of data (i.e. web pages) requested.

In detail, the medical machine is predisposed to be connected to the internet in particular with a fixed IP address such that the web pages thereof are selectively accessible.

A general characteristic of a web server publishing web pages, i.e. an internet website, is that of being available on the internet with a certain degree of continuity for those who need to access the site.

In this sense the connecting of the medical machine could be defined as a permanent connection which denotes the normally-active connection to the internet which characterises web-sites and distinguishes them from convention client serves which, on the contrary, must set up a new connection each time exchange of data is required, with any remote processor.

It is clear that for breakdowns, maintenance or other extremely practical matters, the connection between the machine and the internet can be interrupted, without altering the characteristic of substantial temporal continuity of the connection. The connecting means 16 advantageously comprise an auxiliary memory, predisposed to contain a permanent IP address, independently associated to the medical machine; the IP address is used for the above-mentioned permanent connection to the internet.

A further fundamental characteristics of an internet site is that the server which physically incorporates the contents of the site is identified by an IP address (Internet Protocol) so that the server can be correctly addressed by the various routers and providers constituting the internet.

The IP address is basically constituted by a 32-bit number, for the sake of simplicity usually a sequence of four numbers, each comprised between 0 and 255, and separated from the others by a dot (for example 192.168.9.112).

As indicated, IP addresses are used for identifying the actual physical machines in which the web pages are contained, together with the contents attached thereto, which constitute an internet site.

To enable net users to record the addresses of the various sites, each IP address is usually, but not necessarily, univocally associated to a domain name, i.e. a sort of name or title given to the site and indicating the contents of the site.

At the moment when a net user decides to connect to a predetermined internet site, she or he enters the name of the site or the IP address to be visited in the address bar of her or his browser.

In the case in question, the remote user enters the domain name or the IP address of the machine she or he wishes to contact.

The composition of the domain name constitutes the generation of the request signal; the domain name is immediately converted into the corresponding IP address, such that the request is correctly directed towards the medical machine 2.

This is made possible by the structure of the internet, internally of which the various nodes are able, via a series of pre-stored tables, to direct the signals to the pre-selected address.

A first table enables the addressee's IP address to be found, if the domain name associated thereto is known; the subsequent tables set up the distance link between the remote processor 7 and the medical machine, appropriately selecting the branches of the net to be used for the transmission.

Finally, a last database associates the IP address to a branch which is directly connected to the addressee computer, such that the data can be sent to it.

In the light of the above, it is clear how the dedicated association of a permanent IP address to the medical machine enables the machine to be visible to the users on the internet, and in particular the doctor, technician or remote user, to all effects just like a website which can be accessed independently of the physical position of the remote processor 7.

In some cases, for example, when the various servers and providers reorganise their internal databases with the aim of optimising the exploitation of the hardware and software resources and rendering net operation as efficient and possible, IP addresses associated to each site can be changed; this does not mean however that the IP address combined with a predetermined internet site cannot be defined as permanent, differently to the provisional code attributed to normal clients each time the client accesses the net via its provider.

The web pages provided (contained or generated in real-time) in the web server 11 of the medical machine are consultable via a web browser 18, i.e. a program which enables the users to view and interact with texts, images and other data contained in one or more web pages of a web server.

The web browser 18 is generally able to interpret the HTML code and display it in the form of a hypertext, enabling surfing of the web server pages.

The web server 11 in the medical machine 2 will be accessible via standard-type web browsers 18, commonly used for surfing the internet.

By way of example, the following browsers can be used: Internet Explorer, Mozilla Firefox, Opera or others besides, for access to the web server of each of the medical machines.

Usually, and advantageously, web pages of the web server comprise the client control software 14 such that it does not necessary have to be resident or have been downloaded previously on the remote processor for access to the medical machine.

Obviously the control software could be a compiled program, resident on the web page of the web server of the medical machine, for downloading, installing on the remote unit and thereafter being usable; however it has been found to be particularly advantageous to upload the program to the web page in the form of a specific language, for example a scripting language or an interpreted programming language (i.e. which is not compiled)—destined in general for use in system automation (batch) or applications (macros), or for use in the web pages.

Examples of scripting languages are JavaScript, VBScript, Shell scripting (Unix), Perl, PHP, Python e Ruby.

An example of an interpreted language is JavaApplets.

All of the above means that the client program 14, in scripting language or interpreted language, is directly and automatically executed (interpreted) by the web browser 18 without any need for intervention on the part of the user.

Having directly provided the web server 11 with the VNC client software 14 constitutes a considerable simplification of the monitoring and control procedures.

It should be noted that at least one of the web pages of the medical machine 2 reproduces the graphic user interface shown on the display 6 of the machine itself, apart from a plurality of further data and information relating to the medical machine.

In more detail, thanks to the remote access and control means 10 (which comprise the VNC server and the VNC client), the graphic user interface shown on the display 6 is reproduced in the web pages of the web server 11 and the reproduction is done practically in real-time.

In other words, the reproduction of the graphic user interface is updated at each predetermined time interval and/or at each predetermined change of at least a parameter represented in the graphic user interface itself.

The above-mentioned update of the graphic user interface can also be done as follows, with the aim of reducing the amount of work done by the controller. The display is subdivided into a plurality of regions (distinct monitoring regions) in which each region of the display is subjected to a monitoring; each time a change in the information reproduced in a certain region of the screen occurs, the update only for that region is sent.

The user can therefore, for example by means of an authentication with a password or similar authentication systems, access the web pages of the medical machine, receive a graphic representation which substantially coincides and is in real-time with the graphic representation of the user interface or GUI, and can also surf between the cited plurality of further data published in the web pages of the web server 11, such as for example information relating to the configuration of the machine (version of the programs loaded, cards installed on-board, etc.).

The user can also access the pages for data relating to maintenance (days since last check, or until next maintenance operation).

The user can receive information relating to the replacement of the ultrafilter (days since the last or before the next replacement of the ultrafilter, number of disinfection operations carried out since the last replacement, etc.).

Time/variation graphs can be viewed for some predetermined parameters, so that their progress can be monitored.

Access might be given to the alarm record of the machine (for example the last N alarms, the most frequent alarms, etc.).

Access can be given to data relating to the dates of disinfections performed on the machine, as well as to the history of control tests done by the machine in the context of preventive maintenance, as will be more fully described herein below. As however previously mentioned, the remote access and control means 10 are not exclusively dedicated to enabling secure access to a plurality of data relating to the medical machine, but have also the function of enabling selective control of at least a predetermined number of functions of the machine itself.

The controllable functions of the medical machine are multiple and can comprise, purely by way of example, pump velocity, heparin doses (or other substances), treatment operating parameters, such as the treatment times of the rate of ultrafiltration; further, among the controllable functions are the internal check or diagnostic check procedures, as are the updating or downloading of programs onto the machine.

In a non-exclusive preferred embodiment, the remote access and control means 10 enable the remote control unit 7 to take over complete control of the medical fluid treatment machine 2 such that a remote user can interact with the machine as if she or her were actually standing in front of the machine 2 controls.

Generally, for each remote connection, the user will have to be identified and the authentication will be done for example by means of entering the identification and corresponding password. In any case remote identification might be done in different ways, possibly even in combination, and according to the required level of security. Identification systems can be used such as cards with chips, or contactless, means for biometric recognition (fingerprints, iris recognition or the like), or others besides.

In any case, at least an ID datum must be included among the data exchanged by the medical machine 2 with the remote unit, perhaps for example by the control unit 4 (but also from the web server 11 or even from the central control program 12).

The machine 2 will include a list of predefined identification data, to each item of which a respective access authorisation to the medical machine will be associated.

The access authorisations define the remote interventions the user can make on the medical machine. They comprise at least the authorisation to passive access to vision, i.e. to be allowed to view the web pages of the web server 11 without however being able to control any machine 2 functions, and at least permission to actively access in order to control, i.e. to actively control (i.e. change or set machine operating parameters or activate/deactivate functions) from a remote location.

In reality the access levels can be many, and can be easily customised such that each user can only view and/or intervene on the machines 2 to pre-decided extents.

Some users might only be authorised to view the GUI, while others might be authorised to view all machine data but without any authority to intervene. Others besides might have active control access only to some machine functions and not others, while still others might have total access to all machine functions both passively (viewing) and actively (controlling).

Thus levels of access can be defined, for example for medical personnel, nurses, technical staff controlling and maintaining the machine, or net system administrators.

On each connection, after the ID procedure, the control unit 4 (or as mentioned the web server 11 or the central control program 12) will verify access authorisation and will assign the user the level of access afforded to him or her. In other words, according to the type of protected access afforded, the remote user will be able to operate at least in a solely monitoring mode (having access to all the above-mentioned data without any power to interact actively with the medical machine) and a full machine control mode (where she or he will be able to interact and command the medial machine as if standing right before it).

Obviously situations can be set up in which there is only a partial control modality, i.e. only some of the functions normally controlled by acting directly on the machine.

Note however that the control unit 4 of the medical machine is predisposed to selectively inhibit the remote access and control means 10 from taking and/or maintaining control of at least some of the predetermined number of medical machine functions in particular not only according to the ID of the user, but also (or even only) according to the operating configuration (or modality) of the machine itself.

In other words the medical machine 2 will operate in a plurality of different operating configurations (or modes), some of which will be more or less critical for security.

With reference to known-type medical machines for extracorporeal blood treatment, some of the above-mentioned various operating configurations can be described: at least a first operating configuration for machine start-up and automatic check of its operability; a priming operating configuration of the hydraulic circuit, which consists in the preparatory stage of the machine before treatment in which air is removed from the piping; a disinfecting/cleaning operating configuration (for example chemical and/or thermal) of the hydraulic circuit; a rinsing operating configuration of the hydraulic circuit; an operating configuration in which treatment fluid is prepared (for example a dialysis fluid) up to reaching the desired characteristics of the fluid, etc.

There is also an operating configuration in which the medical machine is set up for use, i.e. all single-use disposable components are applied, such as the filter and the blood circuit. There is also a blood circuit priming operating configuration, and configurations for other disposable circuits too.

There is also an operating configuration of connecting the patient to the machine and a treatment configuration followed by the patient blood return operating configuration (rinseback) after finishing the treatment, and finally the disconnection of the patient.

Further machine configurations can be identified, i.e. a configuration in which the disposable components are removed, or one in which the liquids still present in the circuits are eliminated, as well as other operating configurations connected with various further procedures such as calibrations, maintenance or more besides.

Merely by way of example the critical operating configurations for questions of security are the stage of connecting and the stage of disconnecting the patient to and from the machine before and after treatment, as well as the stage of treatment true and proper and the stage of rinse-back, in which the residual blood is returned to the patient.

Should the control unit 4 detect that the machine is in one of the operating configurations defined as critical for security, the control unit itself would be empowered to prevent the remote means for access and control 10 to take control of the medical machine or, in a case in which a remote unit 7 is controlling, the control unit 4 would exclude any possibility of proceeding with said control/intervention from remote.

All of the above is true whatever the type of the individual in remote connection (doctor, technician, etc. . . . )

Thus according to the operative configuration, the control unit 4 is automatically able to detect a situation of potential danger and will prevent access by a remote user whatever her or his authorisation level.

This mode of operation thus enables potentially dangerous situations to be accounted for, in which sending commands to the machine would be preferable or it would be physically necessary to be present in the place where the medical machine is located in order to take account of situations which cannot be perceived from a remote position (interactions with the patient such as disconnection or connection, or the state of the patient during treatment etc.).

It should be noticed that in general, in order to be able fully to exploit the above-described functionalities, the remote unit 7 will be provided with a respective device 8 for entering at least command data (in this case too it might be a keyboard, a mouse or a touch screen or another suitable system) and also a display screen 9 for viewing at least a part of the information relating to the fluid treatment means 3 and in general the graphic user interface substantially in real-time (i.e. with transmission delays of a few seconds).

Obviously there will be connecting means 16 present for setting the remote unit 7 in communication with the medical machine 2 for fluid treatment for exchange of data.

In general the connecting means 16 are of known type and comprise a computer network, for example an internet network and/or an Ethernet and/or a wireless network, for setting the remote unit 7 (any unit 7 connected to the network) in communication with a the means for fluid treatment 2 (i.e. the desired machine from among all the machines connected up to the network and therefore accessible).

The means 16 shall be provided with receiving and transmitting modules able to receive a request signal coming from the remote unit 7 and transmitting, following the reception, a transmission signal destined for the remote processor and incorporating the data and/or one or more of the web pages present on the web server 11 managed by the processing unit 4.

To this end there will also be special communication ports, network cards and/or modems not further described herein inasmuch as they are of absolutely known type in the sector.

The invention provides important advantages.

The use of Virtual Network Computing programs or the like, such as for example VNC server and VNC client programs, means remote users can accede to and monitor all the necessary machine information; security is in all cases extremely high because the control of the medical machine is not exclusive but filtered by the microprocessor mounted on board the medical machine which can discern both the authorisation level and the intervention level for the subject accessing from a remote position, and can also distinguish the critical operating configurations for security at which all possibility of external control is inhibited.

This final operation is performed automatically and immediately, preventing any dangerous situations from arising, especially for the patient.

Further, the present of a web server on the machine for extracorporeal blood treatment enables a remote access by means of the use of standard electronic processors or handheld processors without any need for installing additional software or for have special ICT skills.

Further, the presence of the VNC client software (in scripting or interpreting language) directly in the web pages of the web server, can be interpreted by common web browsers, even on different operating platforms and systems (such as for example Linux, Windows, and the like).

Access via security levels (for example by password) enables both exclusive monitoring of the dialysis machine and, possibly, a selective remote control such as to be able to perform routine operations including maintenance, intervention on the part of a health operative or a doctor or a technician, without any need to actually go to the machine or machines location.

Figure 3:
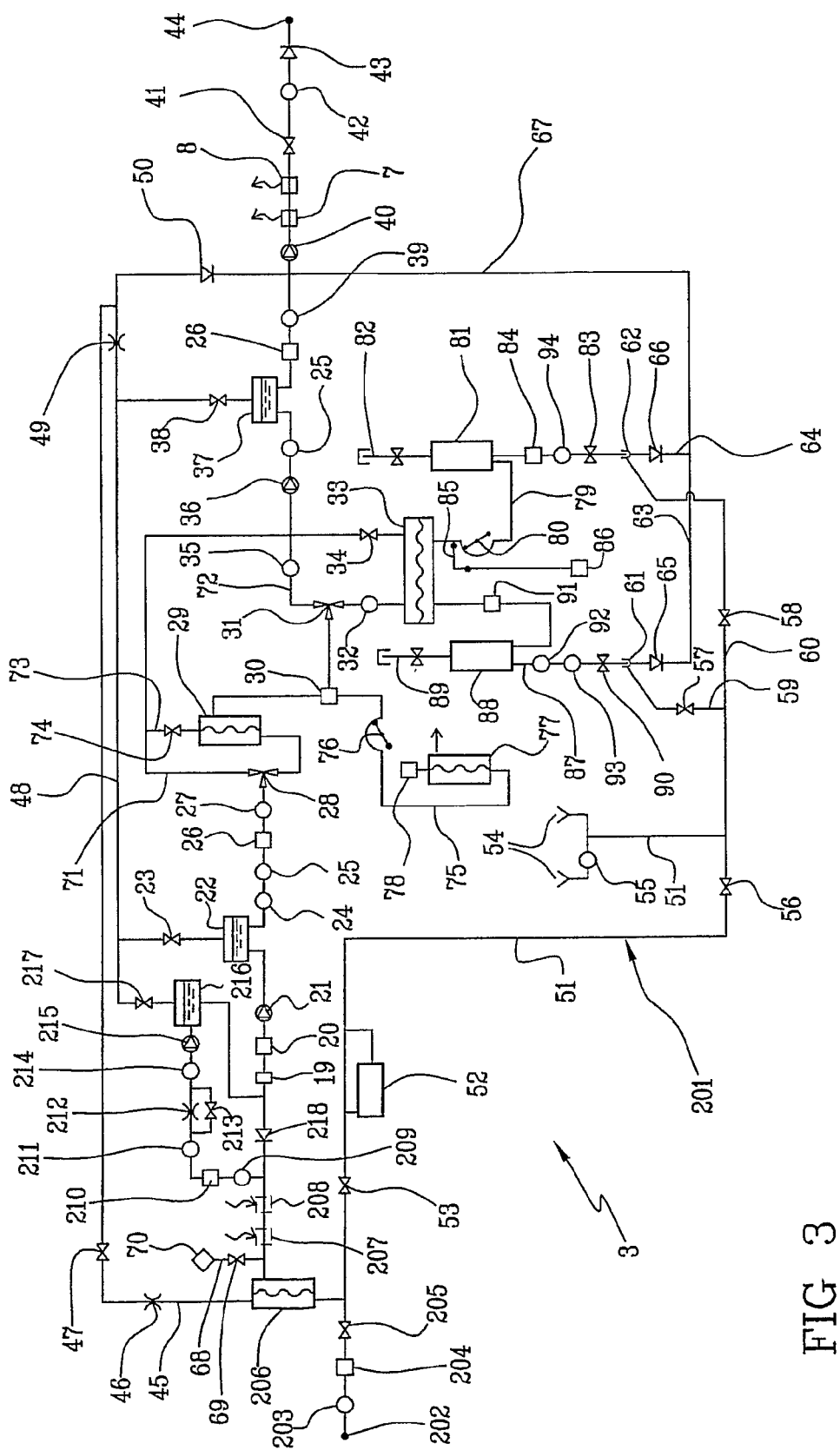
FIG. 3 is a schematic view by way of example of a second embodiment of the means for treatment of a fluid, part of the medical machine of FIG. 1.

The following is the legend for FIG. 3.
201 Hemodiafiltration apparatus
202 Water inlet
203 Inlet pressure sensor
204 Inlet pressure regulator
205 Inlet check valve
206 Ultrafilter for water at inlet
207 First heat exchanger
208 Second heat exchanger
209 Pressure sensor at inlet of the heating and degassing circuit
210 heater
211 temperature sensor in the heating and degassing circuit
212 degassing choke
213 bypass valve of degassing choke
214 pressure sensor for control of degassing pump
215 degassing pump 216 first gas-liquid separator in heating and degassing circuit
217 first degassing valve
218 check valve for the heating and degassing circuit
19 pressure regulator at outlet of heating and degassing circuit
20 on-line preparation device for dialysate with water and concentrates
21 fresh dialysate movement pump
22 second gas-liquid separator for the fresh dialysate
23 second degassing valve
24 sensor system for measuring some parameters (in particular temperature, conductivity and pH) of the fresh dialysate
25 protection system for fluid balance in excess in control system
26 fluid balance control system
27 pressure sensor at inlet of dialysate ultrafilter
28 first bypass valve for bypass of dialysate ultrafilter
29 dialysate ultrafilter
30 connection for a disposable line for replacement fluid
31 second bypass valve for dialyser bypass
32 pressure sensor at dialyser inlet
33 dialyser
34 check valve at dialyser outlet
35 pressure sensor at dialyser outlet
36 used dialysate movement pump
37 third gas/liquid separator for used dialysate
38 third degassing valve
39 sensor system for measuring some parameters (in particular temperature, conductivity, pressure and presence of blood loss) of the used dialysate
40 aspiration pump for stabilising pressure downstream of the fluid balance control system
41 normally-open check valve at outlet
42 outlet pressure sensor
43 outlet check valve
44 outlet end connected to a drainage
45 water ultrafilter flushing line
46 flushing line choke
47 check valve on flushing line
48 breather valve connected to the breathers of the various gas-liquid separators
49 choke connected to the breathers of the various gas-liquid separators
50 check valve operating on a tract of line in common with the flushing line and the breather circuit
51 recycling circuit for complete thermal or chemical disinfection circuit
52 source of a chemical disinfectant including the means for supplying the disinfectant
53 first check valve for enabling recycling during thermal or chemical disinfection
54 pair of connectors for dialyser bypass during thermal or chemical disinfection
55 dialyser bypass flow sensor
56 second check valve to enable recycling during thermal or chemical disinfection
57 first check valve for enabling supply of disinfectant to the first discharge port of the priming fluid
58 second check valve for enabling supply of disinfectant to the second discharge port of the priming fluid
59 first branch for disinfection of the first discharge port of the priming fluid
60 second branch for disinfection of the first discharge port of the priming fluid
61 first discharge port of the priming fluid
62 second discharge port of the priming fluid
63 first discharge line of priming fluid
64 second discharge line of priming fluid
65 first check valve
66 second check valve
67 line conjoining the first and second priming fluid discharge lines with the used dialysate line
68 line connecting with the atmosphere upstream of the heating and degassing circuit
69 check valve of the connecting line with the atmosphere
70 air filter
71 first bypass line (dialysate ultrafilter bypass)
72 second bypass line (dialyser bypass)
73 flushing line of the dialysate ultrafilter
74 check valve of the dialysate ultrafilter flushing line
75 replacement fluid supply line
76 replacement fluid movement pump
77 replacement fluid pump ultrafilter
78 replacement fluid breather system
79 arterial line
80 blood pump
81 arterial chamber
82 arterial chamber service line
83 arterial clamp
84 arterial line access site
85 anticoagulant supply line
86 anticoagulant source
87 venous line
88 venous chamber
89 venous chamber service line
90 venous clamp
91 venous line access site
92 air bubble sensor
93 blood presence sensor (patient sensor)
94 hemoglobin or hematocrit sensor, or blood volume sensor.

The invention claimed is:

1. A medical apparatus comprising at least a medical machine for fluid treatment configurable in a plurality of operating configurations, the medical machine exhibiting:
   means for treating a fluid including a predetermined number of sensors for detecting functioning parameters of the medical machine and a predetermined number of actuators for intervening in order to modify functioning parameters of the medical machine;
   a control unit at least for sending command signals and for receiving information from the means for treating a fluid, the control unit sending command signals to the actuators and receiving data from the sensors in order to set the operating configuration of the machine;
   a device for entering data to be supplied to the control unit for enabling a user to generate the command signals for the means for treating a fluid;
   a display for viewing at least a part of the information received from the control unit relating to the means for treating a fluid;
   remote access and control means for enabling a remote control unit to take control of a predetermined number of functions of the medical machine for treatment of a fluid, the remote access and control means being configured to receive in input at least one identification datum coming from the remote control unit, the control unit of the medical machine being configured to selectively enable or inhibit the remote access and control means from taking control of at least a part of the predetermined number of functions of the medical machine according to the at least one identification datum received;

wherein the control unit of the medical machine is further configured so that (a) if control has been granted to the remote access and control means and (b) if the medical machine is thereafter in a preselected operating configuration, the control unit can selectively inhibit the remote access and control means from maintaining said control of at least a part of one or more of the predetermined number of functions of the medical machine whereby the remote access and control means loses said control of said at least a part of one or more of the predetermined number of functions of the medical machine.

2. The apparatus of claim 1, wherein the plurality of operating configurations comprise one or more operating configurations critical for security, and wherein the control unit inhibits the remote access and control means from taking control of the predetermined number of functions of the medical machine at least when the medical machine is configured in an operating configuration critical for security.

3. The apparatus of claim 2, wherein the one or more operating configurations critical for security are selected from a group consisting of a configuration in which a patient is connected to the medical machine, a treatment configuration, a blood return configuration to the patient at end of treatment, and a disconnecting configuration of the patient from the machine.

4. The apparatus of claim 1, wherein the remote access and control means enable the remote control unit to take complete control of all the functions of the medical machine for fluid treatment in operating configurations in which the control unit does not inhibit the control means from maintaining control of the medical machine.

5. The apparatus of claim 4, wherein in the operating configurations in which the control unit does not inhibit the control means from maintaining control of the medical machine, a remote operator can send, via a device for entering command data of a remote control unit, same command signals as those which can be sent by means of the device for entering data belonging to the medical machine.

6. The apparatus of claim 1, wherein the medical machine further comprises a web server operatively cooperating with the control unit and configured for publishing a predetermined number of web pages, the web pages being remotely accessible by connecting means and being consultable via a web browser, the web server being configured to receive in input the at least an identification datum coming from the remote control unit.

7. The apparatus of claim 1, wherein the medical machine comprises a list of predefined identification data, each of which identification data being assigned respective access faculties to the medical machine, the control unit comparing the identification datum received with the predefined list of identification data in order to establish a correspondence, and once the correspondence has been established, selectively enabling the remote access and control means to take control of a predetermined number of functions of the medical machine for fluid treatment according to the associated access faculty.

8. The apparatus of claim 7, wherein the faculties of access comprise at least a passive faculty of viewing access and an active faculty of control, the remote access and control means taking control of a predetermined number of functions of the medical machine for fluid treatment should the identification datum received correspond to an identification datum in the predefined list which datum is associated to the active faculty of control access and wherein the control unit inhibits the remote access and control means from taking control of the predetermined number of functions of the medical machine for fluid treatment when the identification datum received corresponds to an identification datum in the predefined list associated to the faculty of passive access of viewing.

9. The apparatus of claim 1, wherein the remote access and control means comprise at least a central control program configured to allow remote administration of the predetermined number of functions of the medical machine.

10. The apparatus of claim 9, wherein the medical machine comprises at least a memory store which cooperates with the control unit, the central control software being resident in the memory store in order to be used by the control unit.

11. The apparatus of claim 9, wherein the remote access and control means further comprise a client control program, the client control program being configured to interact with the central control software in order to enable an exchange of data between the control unit and the remote control unit.

12. The apparatus of claim 11, wherein the central control program is a VNC server and the client control program is a VNC client.

13. The apparatus of claim 1, further comprising at least a remote unit for distance control of the medical machine for fluid treatment, the remote control unit exhibiting:
a device for entering at least command data;
a display for viewing at least a part of data relating to the fluid treatment means;
a processing unit for receiving the command data from the entering device and sending them via the remote access and control means and the connecting means, to the control unit of the medical machine.

14. The apparatus of claim 13, wherein the remote control unit comprises at least a memory cooperating with the processing unit, the client control program being resident in the memory.

15. The apparatus of claim 1, wherein the display of the medical machine shows, in use, a graphic user interface configured to show, in an intuitively-understandable form, at least a part of the data received from the control unit relating to the means for fluid treatment and wherein the remote access and control means enable a reproduction on the display of the remote control unit of the graphic user interface shown by the display of the medical machine.

16. The apparatus of claim 15, wherein reproduction of the graphic user interface on the display of the medical machine and on the display of the remote control unit is substantially done contemporaneously.

17. The apparatus of claim 1, further comprising connecting means which set in communication, for exchange of data, the remote control unit with the medical machine for fluid treatment, wherein the connecting means are chosen in a group comprising a computer network, an internet network, an Ethernet network and a wireless network, in order to set the remote control unit in connection with the machine for fluid treatment.

18. The apparatus of claim 1, wherein the medical machine further comprises a web server which operatively cooperates with the control unit and a predetermined number of web pages published by the web server, the web pages being remotely accessible by connecting means and being consultable by means of a web browser, at least a web page reproducing a graphic user interface shown on the display of the medical machine, the web pages further publishing a plurality of further data relating to the medical machine.

19. The apparatus of claim 18, wherein the web server is an internet web server consultable remotely by means of a web browser and wherein the remote access and control means enable reproduction of the web pages in the web server of a graphic user interface shown on the display.

20. The apparatus of claim 19, wherein the remote access and control means enable reproduction of the graphic user interface in the web pages, substantially in real-time, the reproduction of the graphic user interface being updated at each predetermined time interval.

21. The apparatus of claim 19, wherein the remote access and control means enable reproduction of the graphic user interface in the web pages, substantially in real-time, the reproduction of the graphic user interface being updated at each predetermined variation of at least a parameter represented in the graphic user interface.

22. The apparatus of claim 21, wherein the graphic user interface is subdivided into a plurality of regions and in that the updating of the reproduction of each region of the graphic user interface is performed at each predetermined variation of at least a parameter shown in the region, without updating the regions where the predetermined variation has not taken place.

23. The apparatus of claim 18, wherein the remote access and control means comprise at least a central control program and at least a client control program, the client control program being destined to interact with the central control program in order to enable an exchange of data between the control unit and the web server such that the graphic user interface shown on the display can be reproduced in the web pages.

24. The apparatus of claim 23, wherein the web pages of the web server comprise the client control program.

25. The apparatus of claim 23, wherein the client control program is not resident in, or downloaded by, a remote control unit for access to the graphic user interface of the web pages of the web server.

26. The apparatus of claim 23, wherein the client control program resides in the web pages of the web server in a language interpretable by a web browser.

27. The apparatus of claim 23, wherein the client control program resides in the web pages of the web server in a form of a scripting language.

28. The apparatus of claim 18, wherein the plurality of further data published on the web pages of the web server comprises data chosen in the group including data relating to maintenance of the medical machine, data relating to configuration of the medical machine, data relating to a history of alarms issued by the medical machine, data relating to a history of the disinfection operations performed on the medical machine, data relating to a history of functionality checks performed on the medical machine, graphs relating to time and evolution of predetermined parameters of the medical machine.

29. A method for remotely accessing and controlling a medical machine for treatment of fluids, the medical machine being configurable in a plurality of different operating configurations, the method comprising the following stages:
   predisposing at least a medical machine for treatment of fluids, exhibiting:
   means for treatment of a fluid including a predetermined number of sensors for detecting functioning parameters of the medical machine and a predetermined number of actuators for intervening in order to modify functioning parameters of the medical machine;
   a control unit configured at least to send command signals and receive information from the means for treatment of fluids, the control unit sending command signals to the actuators and receiving data from the sensors in order to set the operating configuration of the machine;
   a device for entering data to be supplied to the control unit in order to enable a user to generate the command signals for the means for treatment of fluids;
   a display for viewing at least a part of the data received from the controlled unit relating to the means for treatment of the fluid;
   remote access and control means for enabling a remote control unit to take over control of a predetermined number of functions of the medical machine for treatment of fluid;
   predisposing at least a remote control unit for distance-control of the medical machine for treatment of fluids, exhibiting:
   a device for entering at least command data;
   a display for viewing at least a part of the data relating to means for treatment of fluid;
   setting the remote control unit in communication with the medical machine for treatment of fluids via connecting means for an exchange of data and for receiving in input at least one identification datum coming from the remote control unit;
   comparing, via the control unit of the medical machine, the at least one identification datum received with a list of predefined identification data, each of the identification data being assigned with respective faculties of access to the medical machine;
   establishing a correspondence between the at least one identification datum received and the predefined list of identification data and associating a respective access faculty;
   selectively enabling or inhibiting the remote access and control means to take control of a predetermined number of functions of the medical machine for treatment of fluids according to the at least one identification datum or according to the associated access faculty;
   establishing the operative configuration of the medical machine via the control unit using the data received from the means for treatment of the fluid;
   remotely controlling the medical machine by means of the remote control entering command data via the entering device, the connecting means enabling transmission of the command data and the remote access and control means enabling the remote control unit to take control of a predetermined number of functions of the medical machine for treatment of a fluid;
   comparing the predetermined operating configuration in order to establish whether the predetermined operating configuration belongs to a predetermined group of operating conditions, critical for security;
   in a case in which the medical machine is in an operating condition belonging to a group of the critical operating conditions for security, inhibiting the remote access and control means from taking or maintaining control of the predetermined number of functions of the medical machine and the remote access and control means losing said control of one or more of the predetermined number of functions of the medical machine.

30. The method of claim 29, wherein the access faculties comprise at least a passive access to viewing and an active access to control, the remote access and control means taking control of a predetermined number of functions of the medical machine for treatment of fluid should the identification datum received correspond to an identification datum of the predefined list associated to the active access to control faculty.

31. A medical apparatus comprising at least a medical machine for fluid treatment configurable in a plurality of operating configurations, the medical machine exhibiting:

means for treating a fluid including a predetermined number of sensors for detecting functioning parameters of the medical machine and a predetermined number of actuators for intervening in order to modify functioning parameters of the medical machine;

a control unit at least for sending command signals and for receiving information from the means for treating a fluid, the control unit sending command signals to the actuators and receiving data from the sensors in order to set the operating configuration of the machine;

a device for entering data to be supplied to the control unit for enabling a user to generate the command signals for the means for treating a fluid;

a display for viewing at least a part of the information received from the control unit relating to the means for treating a fluid;

remote access and control means for enabling a remote control unit to take control of a predetermined number of functions of the medical machine for treatment of a fluid, the remote access and control means being configured to receive in input at least one identification datum coming from the remote control unit, the control unit of the medical machine being configured to selectively enable or inhibit the remote access and control means from taking control of at least a part of the predetermined number of functions of the medical machine according to the at least one identification datum received;

wherein the control unit of the medical machine is further configured so that (a) if control has been granted to the remote access and control means and (b) if the medical machine is thereafter in a preselected operating configuration, the control unit can selectively inhibit the remote access and control means from maintaining said control of at least a part of one or more of the predetermined number of functions of the medical machine whereby the remote access and control means loses said control of said at least a part of one or more of the predetermined number of functions of the medical machine, and wherein the plurality of operating configurations comprises two or more of:

an operating configuration for start-up of the medical machine, an operating configuration for conducting an operability check of the medical machine, an operating configuration for setup, preferably comprising application of single-use disposable components to the medical machine, an operating configuration for priming, an operating configuration for preparation of treatment fluid, an operating configuration for connecting a patient to the machine, an operating configuration in which the patient is connected to the medical machine, an operating configuration for treatment, an operating configuration for returning blood to the patient, an operating configuration for disconnecting the patient from the machine, an operating configuration for rinsing, an operating configuration for disinfection, an operating configuration for cleaning.

32. The apparatus of claim 31, wherein the control unit inhibits the remote access and control means from taking control of at least a part of the predetermined number of functions of the medical machine at least in the following operating configurations:

an operating configuration for preparation of treatment fluid, an operating configuration for connecting a patient to the medical machine, an operating configuration in which the patient is connected to the medical machine, an operating configuration for treatment, an operating configuration for returning blood to a patient, an operating configuration for disconnecting the patient from the medical machine.

33. A medical apparatus comprising at least a medical machine for fluid treatment configurable in a first set of operating configurations and in a second set of operating configurations, the medical machine having a current operating configuration, the medical machine exhibiting:

means for treating a fluid including a predetermined number of sensors for detecting functioning parameters of the medical machine and a predetermined number of actuators for intervening in order to modify functioning parameters of the medical machine;

a control unit at least for sending command signals and for receiving information from the means for treating a fluid, the control unit sending command signals to the actuators and receiving data from the sensors in order to set the current operating configuration of the machine;

a device for entering data to be supplied to the control unit for enabling a user to generate the command signals for the means for treating a fluid;

a display for viewing at least a part of the information received from the control unit relating to the means for treating a fluid;

remote access and control means for enabling a remote control unit to take control of a predetermined number of functions of the medical machine for treatment of a fluid, the remote access and control means being configured to receive in input at least one identification datum coming from the remote control unit, the control unit of the medical machine being configured to selectively enable or inhibit the remote access and control means from taking control of at least a part of the predetermined number of functions of the medical machine according to the at least one identification datum received;

wherein the control unit of the medical machine is further configured to selectively:

inhibit the remote access and control means from controlling at least a part of the predetermined number of functions of the medical machine if the current operating configuration of the medical machine is comprised in the second set of operating configurations, and allow the remote access and control means to control the predetermined number of functions of the medical machine if the current operating configuration of the medical machine is comprised in the first set of operating configurations.

34. The apparatus of claim 33, wherein the first set of operating configurations comprises one or more of:

an operating configuration for start-up of the medical machine, an operating configuration for conducting an operability check of the medical machine, an operating configuration for setup, preferably comprising application of single-use disposable components to the medical machine, an operating configuration for priming, an operating configuration for rinsing,
an operating configuration for disinfection,
an operating configuration for cleaning.

35. The apparatus of claim 33, wherein the second set of operating configurations comprises one or more of:
an operating configuration for preparation of treatment fluid,
an operating configuration for connecting a patient to the medical machine,
an operating configuration in which the patient is connected to the medical machine,
an operating configuration for treatment,
an operating configuration for returning blood to a patient,
an operating configuration for disconnecting the patient from the medical machine.

* * * * *